United States Patent

Onizuka et al.

[11] Patent Number: 4,683,210
[45] Date of Patent: * Jul. 28, 1987

[54] METHOD FOR MEASURING CONCENTRATIONS OF $CaCO_3$ AND $CaSO_3$ IN A SLURRY

[75] Inventors: Masakazu Onizuka; Atsushi Tatani; Takayoshi Hamada; Setsuo Omoto, all of Hiroshima, Japan

[73] Assignee: Mitsubishi Jukogyo Kabushiki Kaisha, Tokyo, Japan

[*] Notice: The portion of the term of this patent subsequent to Jun. 30, 2004 has been disclaimed.

[21] Appl. No.: 638,552

[22] Filed: Aug. 7, 1984

[30] Foreign Application Priority Data

Aug. 10, 1983 [JP] Japan .................. 58-144894

[51] Int. Cl.⁴ .............. G01N 1/00; G01N 33/00; G01N 35/00
[52] U.S. Cl. ........................... 436/50; 436/52; 436/55; 436/79; 436/119; 436/133; 436/146; 436/175; 436/179; 436/181
[58] Field of Search .................. 436/43, 50, 51, 52, 436/55, 79, 119, 122, 127, 133, 146, 163, 174, 175, 177, 179, 181

[56] References Cited

U.S. PATENT DOCUMENTS

| | | | |
|---|---|---|---|
| 3,459,938 | 8/1969 | Stenger et al. | 436/146 |
| 3,801,281 | 4/1974 | Thompson et al. | 436/133 X |
| 3,854,876 | 12/1974 | Rankine et al. | 436/133 X |
| 4,046,510 | 9/1977 | Becker et al. | 436/146 |
| 4,061,467 | 12/1977 | Becker et al. | 436/179 X |
| 4,063,891 | 12/1977 | Becker et al. | 436/146 |
| 4,236,960 | 12/1980 | Hultman et al. | 436/55 X |
| 4,397,957 | 8/1983 | Allison | 436/133 |

FOREIGN PATENT DOCUMENTS

| | | | |
|---|---|---|---|
| 0078251 | 6/1980 | Japan | 436/119 |
| 0096450 | 7/1980 | Japan | 436/146 |

Primary Examiner—David L. Lacey
Assistant Examiner—Robert J. Hill, Jr.
Attorney, Agent, or Firm—Birch, Stewart, Kolasch & Birch

[57] ABSTRACT

A method for continuously measuring the concentration of $CaCO_3$ and/or $CaSO_3$ in slurries comprising $CaCO_3$ and/or $CaSO_3$ is described. The method comprises continuouly sampling a given amount of the slurry, feeding the slurry into an agitated continuous reactor container which is isolated from the outside air and in which the slurry is kept at a temperature not lower than 70° C., adding sulfuric acid or hydrochloric acid to the slurry to make the pH below 3, blowing air or nitrogen gas into the slurry in the reactor container, withdrawing from the container $CO_2$ and/or $SO_2$ produced by reaction of $CaCO_3$ and/or $CaSO_3$ with the acid by entrainment with the air or nitrogen gas, and calculating the concentration of $CaCO_3$ and/or $CaSO_3$ from the concentration of $CO_2$ and/or $SO_2$ in the withdrawn gas, the flow rate of the sampled slurry and the flow rate of the blown air or nitrogen gas.

18 Claims, 3 Drawing Figures

FIG. I

METHOD FOR MEASURING CONCENTRATIONS OF $CaCO_3$ AND $CaSO_3$ IN A SLURRY

BACKGROUND OF THE INVENTION

1. Field of the Invention

This invention relates to a method for measuring a concentration of $CaCO_3$ and/or $CaSO_3$ in slurries comprising $CaCO_3$ and/or $CaSO_3$ therein.

2. Description of the Prior Art

Typical of slurries comprising $CaCO_3$ and/or $CaSO_3$ is, for example, an absorption solution used in flue gas desulfurization systems using a wet lime gypsum process. The performance of the flue gas desulfurization system is so controlled that an absorbent such as $CaCO_3$ or $Ca(OH)_2$ is added in amounts sufficient for stoichiometric absorption of $SO_2$ in order to keep the pH of the circulating absorption solution in an absorption tower at a predetermined level.

In recent years, there is the high tendency toward savings of resources or energy and even apparatus which generate exhaust gases such as boilers are now designed to attain high efficiency. In operation, the load variation speed becomes high and thus it will be necessary to follow such a load variation without impeding the performance in the flue gas desulfurization system.

It has been confirmed that in the flue gas desulfurization systems, when the wet lime gypsum process is used, it is difficult to maintain high performance in relation to such a high speed load variation over an entire period by the use of the currently employed pH control system of circulation an absorption solution in an absorption tower. This is because even if the pH of the absorption solution is controlled at a level, the concentration of $CaCO_3$ and/or $CaSO_3$ in the absorption solution varies depending on the variation in the desulfurization load.

The present inventors have extensive studies of a method which can overcome the above difficulties and which can follow the high speed load variation of the exhaust-generating apparatus and maintain good desulfurization performance over an entire period. As a result, it has been found that if a concentration of $CaCO_3$ and/or $CaSO_3$ in absorption solution is known prior to use thereof, it is possible to provide a measure of maintaining the desulfurization performance against the load variation, thus leading to a method of measuring a concentration of $CaCO_3$ and/or $CaSO_3$ according to the invention.

According to the present invention, there is provided a method for continuously measuring the concentration of $CaCO_3$ and/or $CaSO_3$ in slurries comprising $CaCO_3$ and/or $CaSO_3$, the method comprising:

continuously sampling a given amount of the slurry;

feeding the slurry to an agitated continuous reactor container which is isolated from the outside air;

keeping the slurry in the reactor container at a temperature not lower than 70° C. and to which is added sulfuric acid or hydrochloric acid to adjust the pH to below 3;

blowing air or nitrogen gas into the slurry in the reactor container;

withdrawing from the container $CO_2$ and/or $SO_2$ produced by reaction between $CaCO_3$ and/or $CaSO_3$ and the acid by entrainment with the air or nitrogen gas; and calculating the concentration of $CaCO_3$ and/or $CaSO_3$ in the slurry from the concentration of $CO_2$ and/or $SO_2$ in the withdrawn gas, the flow rate of the sampled slurry and the flow rate of the blown air or nitrogen gas.

Moreover, the concentration of $CaCO_3$ and/or $CaSO_3$ in the slurry may be determined by further mixing the withdrawn gas with air or nitrogen gas and calculating the concentration from the concentration of $CO_2$ and/or $SO_2$ in the mixed gas, the flow rate of the sampled slurry, the flow rate of the blow air or nitrogen gas, and the flow rate of the air or nitrogen gas being mixed.

DETAILED DESCRIPTION AND EMBODIMENTS OF THE INVENTION

Figure 1:
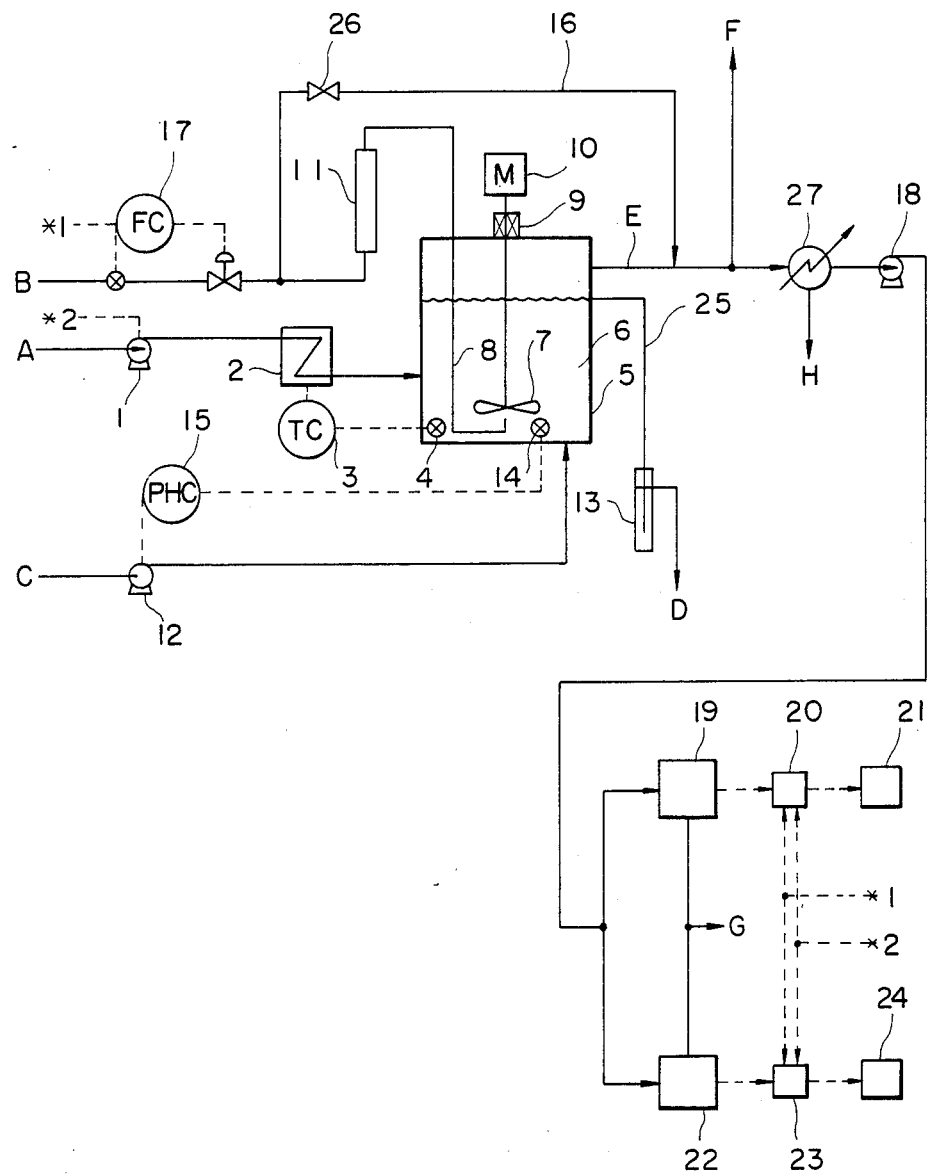
FIG. 1 is a flowchart of a method according to the invention.

Reference is now made to FIG. 1 which illustrates one embodiment of the invention.

In FIG. 1, there is shown a flowchart of a test plant of measuring a concentration of $CaCO_3$ and/or $CaSO_3$ in which indicated at A is a sample solution, at B is air or nitrogen, at C is sulfuric acid (or hydrochloric acid), at D is a waste liquor, at E is a withdrawn gas comprising $CO_2$ and/or $SO_2$, at F is an exhaust, at G is an exhaust, and at H is drain. Moreover, indicated at 1 is a fixed displacement pump, at 2 is a heater, at 3 is a temperature controller, at 4 is a temperature detector, at 5 is an agitated continuous reactor container which is a closed system or is isolated from the outside air, at 6 is a resident liquid, at 7 is an agitator, at 8 is a blowing pipe, at 9 is a sealing material, at 10 is a motor, at 11 is a flow controller, at 12 is a delicate pump, at 13 is a liquid sealing device, at 14 is a pH electrode, at 15 is a pH adjuster, at 16 is air or nitrogen, at 17 is a flow controller, at 18 is an air pump, at 19 is a $CO_2$ analyzer, at 20 is an operator, at 21 is an indicator, at 22 is a $SO_2$ analyzer, at 23 is an operator, at 24 is an indicator, at 25 is an overflow pipe, at 26 is a valve, at 27 is a dehumidifier, and at *1 and *2 are signals.

In operation, sample liquid A comprising $CaCO_3$ and/or $CaSO_3$ is samples by the fixed displacement pump 1 and is heated through the heater 2 in such a way that the resident liquid 6 in the reactor container 5 is raised to a predetermined temperature over 70° C., followed by feeding to the reactor container 5. The heater 2 is controlled by signal from the temperature controller 3 after detection of the temperature of the resident liquid 6 with the detector 4 so that the resident liquid 6 has a predetermined temperature (over 70° C.).

It should be noted that the upper limit of the temperature of the resident liquid 6 is a boiling point of the resident liquid.

The liquid 6 in the reactor container 5 is agitated by means of the agitator 7 so that the solid matters in the liquid 6 do not settle, and the pH of the liquid 6 is checked by the use of the pH detector 14. According to the results of the pH check, the delicate pump 12 is controlled by the signal from the pH adjuster 15. As a result, sulfuric acid (or hydrochloric acid) is introduced into the reactor container 5 and the pH in the system is adjusted to below 3. The pH can be controlled in the range of from 1 to 3.

When sulfuric acid (hydrochloric acid) is introduced into the liquid 6, $CaCO_3$ and/or $CaSO_3$ in the sampled liquid A are reacted ith the acid according to the equations (1) through (4) to generate $CO_2$ and/or $SO_2$.

With sulfuric acid,

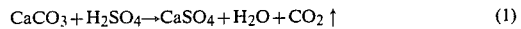

$$CaCO_3 + H_2SO_4 \rightarrow CaSO_4 + H_2O + CO_2 \uparrow \quad (1)$$

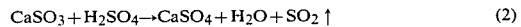

$$CaSO_3 + H_2SO_4 \rightarrow CaSO_4 + H_2O + SO_2 \uparrow \quad (2)$$

With hydrochloric acid,

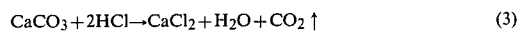

$$CaCO_3 + 2HCl \rightarrow CaCl_2 + H_2O + CO_2 \uparrow \quad (3)$$

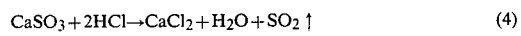

$$CaSO_3 + 2HCl \rightarrow CaCl_2 + H_2O + SO_2 \uparrow \quad (4)$$

The generated $CO_2$ and/or $SO_2$ is removed as follows: part or all of the air (or nitrogen gas) used as a carrier gas whose flow rate has been adjusted by means of the flow adjuster 17 is blown, by operation of the distributing valve 26, into the liquid 6 through the flow indicator 11 and the blowing pipe 8 and the mixture of the $CO_2$ and/or $SO_2$, air (or nitrogen) and moisture are discharged as withdrawn gas E.

On the other hand, the remaining air (or nitrogen) 16 used for the blowing is combined with the gas E discharged from the reactor container 5 and the combined gas is discharged as exhaust F except that part thereof is collected by suction by means of the air pump 18 for use in the $CO_2$ analyzer 19 and the $SO_2$ analyzer 22. It should be noted that the reason why the air 16 is combined with gas E is due to the dilution of the gas E to a concentration detectable by the $CO_2$ analyzer 19.

An excess of the resident liquid 6 involved by the feed of the sample liquid A from the fixed displacement pump 1 is discharged from the overflow pipe 25 into the liquid sealing device 13. The liquid sealing device 13 is kept to have a liquid depth which can overcome the inner pressure in the reactor container 5 and has such a construction that the solid matters contained in the overflow from the reactor container 5 do not settle. An excess of the overflow flown into the liquid sealing device 13 is discharged as waste liquor D.

The withdrawn gas E of the $CO_2$ and/or $SO_2$ generated according to the reaction equations (1) and (2) (or reaction equations (3) and (4)), air (or nitrogen) and moisture is combined, as noted before, with the remaining air (nitrogen) 16, after which it is discharged as exhaust F. Part of the exhaust F is passed into the dehumidifier 27 in which the moisture is removed in drain H, after which it is passed through the air pump 18 into the $CO_2$ analyzer 19 and/or $SO_2$ analyzer 22. In the $CO_2$ analyzer 19 and/or $SO_2$ analyzer 22, the concentration of $CO_2$ and/or $SO_2$ in the exhaust is measured, followed by discharging as exhaust G.

The signals from the $CO_2$ analyzer 19 and/or $SO_2$ analyzer 22 are passed to the operator 20 for the $CaCO_3$ concentration and to the operator 23 for the $CaSO_3$ concentration. To the $CaCO_3$ concentration operator 20 and/or $CaSO_3$ concentration operator 23 are further inputted the flow signal *1 from the air (or nitrogen) flow adjuster 17 and the sampling flow signal *2 of the sample liquid A from the fixed displacement pump 1. These input signals are used in the respective operators 20, 21 to effect the logical operation according to the equations indicated below, by which the concentration of $CaCO_3$ and/or $CaSO_3$ in a respective sample liquid A is outputted to the $CaCO_3$ concentration indicator 21 and/or $CaSO_3$ concentration indicator 24 with the concentration of $CaCO_3$ being indicated on the indicator 20 and the concentration of $CaSO_3$ being indicated on the indicator 24.

Calculation of Concentration of $CaCO_3$:

Concentration of $CaCO_3$ (mol/l) =

$$\left( \frac{CO_2(\%)}{100 - SO_2[\%] - CO_2[\%]} \right) \left( \frac{\text{flow rate of air (or Nitrogen) } [Nl/mi}{22.4[Nl/mol] \times \text{flow rate of sample slurry } [l/min]} \right)$$

Calculation of Concentration of $CaSO_3$:

Concentration of $CaCO_3$ (mol/l) =

$$\left( \frac{SO_2(\%)}{100 - SO_2[\%] - CO_2[\%]} \right) \left( \frac{\text{flow rate of air (or Nitrogen) } [Nl/mi}{22.4[Nl/mol] \times \text{flow rate of sample slurry } [l/min]} \right)$$

EXAMPLE

The apparatus of FIG. 1 was used to measure concentrations of $CaCO_3$ and $CaSO_3$. This is particularly described below.

Figure 2:
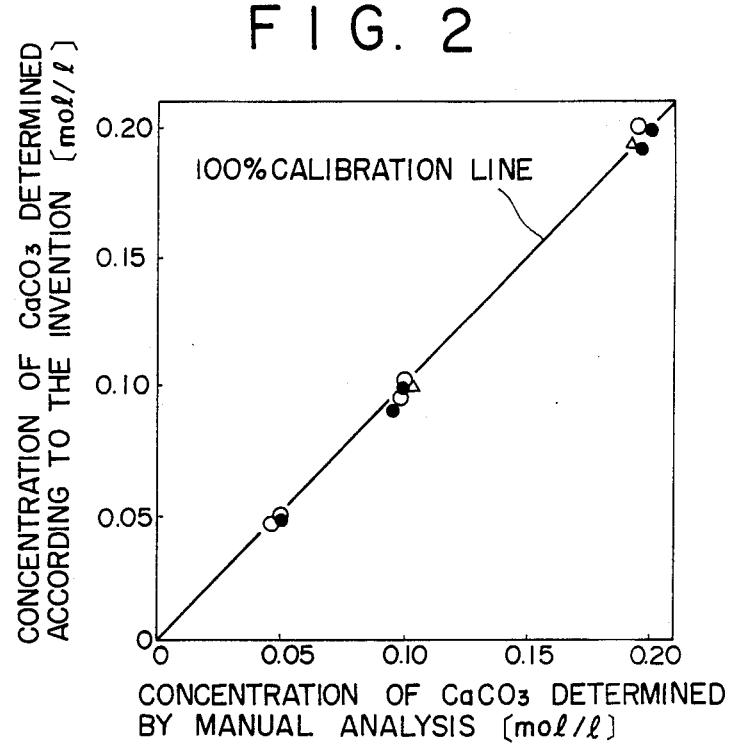
FIG. 2 is a graphical representation of the relationship between measured value of $CaCO_3$ concentration (mol/l) determined according to the method of the invention and value determined by known manual analysis.
Figure 3:
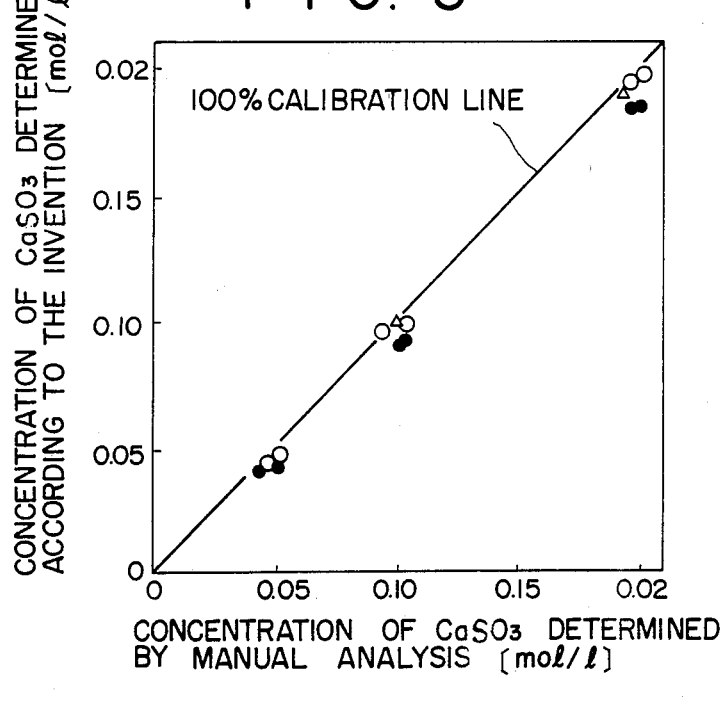
FIG. 3 is a graphical representation of the relationship between measured value of $CaSO_3$ concentration (mol/l) and value measured by known manual analysis.

The test plant of FIG. 1 was used under the following conditions, with the results shown in FIGS. 2 and 3.

Concentration of $CaCO_3$ in sample slurry: 0.05, 0.1, 0.2 mol/l

Concentration of $CaSO_3$ in sample slurry: 0.05, 0.1, 0.2 mol/l

Feed of sample slurry: 0.12 l/min

Kind of carrier gas: air, nitrogen

Flow rate of carrier gas: 20 l/min

Set reaction temperature: 70°, 80° C.

Set pH value in reaction: 3

Flow rate of blown carrier gas: 10 l/min

Capacity of reactor container: 1.5 l.

FIGS. 2 and 3 show graphs of concentrations of $CaCO_3$ and $CaSO_3$ determined according to the method of the invention in relation to values determined by manual analyses. In the graphs, the abscissa indicates concentration of $CaCO_3$ or $CaSO_3$ determined according to the manual analysis and the ordinate indicates concentration of $CaCO_3$ or $CaSO_3$ determined according to the method of the invention. In the figures, the results at 70° C. and 80° C. are indicated by the marks "solid circle" and "circle", respectively, with the results at 80° C. using nitrogen being indicated by the mark "triangle". In the following table are shown some test results concerning measured values of $CO_2$ and $SO_2$, and concentrations of $CaCO_3$ and $CaSO_3$ determined by the manual analyses and the method of the present invention.

TABLE (Carrier gas: air)

| Items and Units | | Case No. 1 | 2 | 3 | 4 | 5 |
|---|---|---|---|---|---|---|
| Reaction temperature | °C. | 70 | 70 | 80 | 80 | 80 |
| Conc. of $CaCO_3$ | mol/l | | | | | |
| manual analysis | | 0.099 | 0.199 | 0.047 | 0.098 | 0.194 |
| inventive method | | 0.098 | 0.198 | 0.048 | 0.095 | 0.199 |
| Conc. of $CaSO_3$ | mol/l | | | | | |
| manual analysis | | 0.044 | 0.102 | 0.052 | 0.103 | 0.196 |
| inventive method | | 0.042 | 0.093 | 0.047 | 0.098 | 0.194 |
| Conc. of $CO_2$ | vol. % | 1.30 | 2.60 | 0.64 | 1.26 | 2.61 |
| Conc. of $SO_2$ | vol. % | 0.56 | 1.23 | 0.63 | 1.30 | 2.54 |
| Type of acid | | HCl | $H_2SO_4$ | $H_2SO_4$ | HCl | $H_2SO_4$ |

As will be seen from the above table, the method of the invention enables one to continuously measure samples of varying concentrations at high speed substantially in the same accuracy as with the case of the manual analyses.

The present invention is described particularly by way of example but should not be construed as being limited to the example. In short, the present invention is characterized as follows: $CaCO_3$ and/or $CaSO_3$ being measured are stoichiometrically converted into $CO_2$ and/or $SO_2$ under certain conditions to determine a concentration of the gas; and the concentration of $CaCO_3$ and/or $CaSO_3$ is measured by operation from the concentration of $CO_2$ and/or $SO_2$.

According to the method of the invention, a concentration of $CaCO_3$ and/or $CaSO_3$ in samples is measurable at high speed and continuously, with attendant advantages that the desulfurization performance corresponding to a load variation at high speed can be maintained and that hands and time can be remarkably saved as compared with those required in manual analysis.

What is claimed is:

1. A continuous method for measuring the concentration of an inorganic compound selected from the group consisting of $CaCO_3$, $CaSO_3$ and mixtures thereof in a slurry containing such an inorganic compound, consisting essentially of:

continuously sampling a given amount of the slurry;
feeding the sampled slurry at a predetermined flow rate into an agitated continuous reactor container having a bottom and which is isolated from outside air;
maintaining the sample slurry in the reactor container at a temperature not lower than 70° C.;
adding an acid to the reactor container to adjust the pH of the slurry therein to below 3, said acid reacting with said inorganic compound to form a reaction product and to generate a gaseous product selected from the group consisting of $CO_2$, $SO_2$ and mixtures thereof, wherein $CO_2$ is generated when the inorganic compound is $CaCO_3$, $SO_2$ is generated when the inorganic compound is $CaSO_3$ and a mixture of $CO_2$ and $SO_2$ is generated when the inorganic compound is a mixture of $CaCO_3$ and $CaSO_3$;
blowing a carrier gas into the slurry in the reactor container at a predetermined flow rate;
withdrawing the carrier gas with the gaseous product entrained therein from the reactor container;
measuring the concentration of the entrained gaseous product in the withdrawn carrier gas; and
determining the concentration of said inorganic compound in the slurry from the concentration of the entrained gaseous product in the withdrawn carrier gas, the flow rate of the samples slurry and the flow rate of the carrier gas, wherein said continuous method is a high speed continuous method capable of measuring the concentration of said inorganic compound in an absorption solution used for pH control of a high speed load variation characterized desulfurization system.

2. The method according to claim 1, wherein the acid is selected from the group consisting of sulfuric acid and hydrochloric acid.

3. The method according to claim 1, wherein the carrier gas is selected from the group consisting of air and nitrogen.

4. The method according to claim 1, wherein the concentration of $CaCO_3$ is determined.

5. The method according to claim 1, wherein the concentration of $CaSO_3$ is determined.

6. The method according to claim 1, wherein the combined concentration of $CaCO_3$ and $CaSO_3$ is determined.

7. The method according to claim 1, wherein the carrier gas is blown into the slurry from the bottom of the reactor container.

8. The method according to claim 1, wherein the slurry in the reactor container is maintained at a temperature in the range of 70° C. to the boiling point of the slurry in the reactor container.

9. The method according to claim 1, wherein the pH of the slurry in the reactor container is adjusted to between 1 and 3.

10. A continuous method for measuring the concentration of an inorganic compound selected from the group consisting of $CaCO_3$, $CaSO_3$ and mixtures thereof in a slurry containing such an inorganic compound, consisting essentially of:

continuously sampling a given amount of the slurry;
feeding the sampled slurry at a predetermined flow rate into an agitated continuous reactor container having a bottom and which is isolated from outside air;
maintaining the sample slurry in the reactor container at a temperature not lower than 70° C.;
adding an acid to the reactor container to adjust the pH of the slurry therein to below 3, said acid reacting with said inorganic compound to form a reaction product and to generate a gaseous product selected from the group consisting of $CO_2$, $SO_2$ and mixtures thereof, wherein $CO_2$ is generated when the inorganic compound is $CaCO_3$, $SO_2$ is generated when the inorganic compound is $CaSO_3$ and a mixture of $CO_2$ and $SO_2$ is generated when the inorganic compound is a mixture of $CaCO_3$ and $CaSO_3$;
blowing a carrier gas into the slurry in the reactor container at a predetermined flow rate;
withdrawing the carrier gas with the gaseous product entrained therein from the reactor container;
adding additional carrier gas to the withdrawn carrier gas with the gaseous product entrained therein at a predetermined flow rate to form a mixture;
measuring the concentration of the entrained gaseous product in the mixture; and determining the concentration of said inorganic compound in the slurry from the concentration of the entrained gaseous product in the mixture, the flow rate of the sampled slurry, the flow rate of the carrier gas and the flow rate of the additional carrier gas, wherein said continuous method is a high speed continuous method capable of measuring the concentration of said inorganic compound in an absorption solution used for pH control of a high speed load variation characterized desulfurization system.

11. The method according to claim 10, wherein the acid is selected from the group consisting of sulfuric acid and hydrochloric acid.

12. The method according to claim 10, wherein the carrier gas is selected from the group consisting of air and nitrogen.

13. The method according to claim 10, wherein the concentration of $CaCO_3$ is determined.

14. The method according to claim 10, wherein the concentration of $CaSO_3$ is determined.

15. The method according to claim 10, wherein the combined concentration of $CaCO_3$ and $CaSO_3$ is determined.

16. The method according to claim 10, wherein the carrier gas is blown into the slurry from the bottom of the reactor container.

17. The method according to claim 10, wherein the slurry in the reactor container is maintained at a temperature in the range of from 70° C. to the boiling point of the slurry in the reactor container.

18. The method according to claim 10, wherein the pH of the slurry in the reactor container is adjusted to between 1 to 3.

* * * * *